United States Patent [19]
Spitz et al.

[11] Patent Number: 5,215,100
[45] Date of Patent: Jun. 1, 1993

[54] NERVE CONDITION MONITORING SYSTEM AND ELECTRODE SUPPORTING STRUCTURE

[75] Inventors: Lawrence K. Spitz, Philadelphia, Pa.; Scott Jaeger, Haddonfield, N.J.; Scott N. Musser, Lebanon, Pa.

[73] Assignee: Occupational Preventive Diagnostic, Inc., Philadelphia, Pa.

[21] Appl. No.: 692,930

[22] Filed: Apr. 29, 1991

[51] Int. Cl.$^5$ .................................................. A61B 5/05
[52] U.S. Cl. ..................................... 128/741; 128/639; 128/420.5
[58] Field of Search ............... 128/741, 733, 734, 744, 128/774, 877, 878, 879, 639, 796, 89 R, 783, 736, 739, 800, 802, 755, 905, 421, 420 A, 420.5; 374/142

[56] References Cited
U.S. PATENT DOCUMENTS

| | | | |
|---|---|---|---|
| 3,043,291 | 7/1960 | Nielsen | 128/377 |
| 4,064,870 | 12/1977 | Dumitrescu et al. | 128/741 |
| 4,387,723 | 6/1983 | Atlee, III et al. | 128/734 |
| 4,517,983 | 5/1985 | Toyosu et al. | 128/639 |
| 4,595,018 | 6/1986 | Rantala | 128/733 |
| 4,807,643 | 2/1989 | Rosier | 128/741 |
| 4,817,628 | 4/1989 | Zealear et al. | 128/741 |
| 4,873,968 | 10/1989 | Finnieston et al. | 128/87 R |
| 4,941,460 | 7/1990 | Working | 128/77 |
| 4,978,335 | 12/1990 | Arthur, III | 604/67 |
| 5,002,065 | 3/1991 | LaCourse et al. | 128/739 |
| 5,023,785 | 6/1991 | Adrion et al. | 364/413.08 |
| 5,033,469 | 7/1991 | Brodard | 128/421 |

OTHER PUBLICATIONS

U.S. Department of Health and Human Services, NIOSH, "Performing Motor And Sensory Neuronal Conductive Studies In Adult Humans", Sep. 1990, pp. i-vi, 1-15, 44-45.

Cadwell Laboratories, Inc., "The Cadwell 5200A Operator's Manual":, Jun. 1988, pp. 3-10, 13, 66-71, TS1-TS12.

Ernest W. Johnson, M.D., "Practical Electromyography", 1980, pp. 16-34, 61-64, 73-82.

Dong M. Ma, M.D. and Jay A. Liveson, M.D., "Nerve Conduction Handbook", 1983, pp. 92-140.

*Primary Examiner*—Max Hindenburg
*Assistant Examiner*—Guy V. Tucker
*Attorney, Agent, or Firm*—Reed Smith Shaw & McClay

[57] ABSTRACT

A portable system for substantially automated monitoring of nerve conduction velocity through the carpal tunnel of a patient includes an electrode supporting structure which supports stimulating and pickup electrodes in a predetermined spatial relationship so as to contact the patient's arm and hand. The electrode supporting structure is a part of a housing which contains stimulating signal generating and response signal processing circuitry, which operates substantially automatically under control of a microprocessor. The microprocessor controls generation of stimulating pulses and determines the elapsed time until the occurrence of a predetermined response signal characteristic, such as its peak. Data relating to nerve conduction time or velocity measurements and response signal waveform are stored in a removable memory to permit later analysis and treatment recommendation by a physician. The system is useful for screening large groups of people at remote locations, such as workers at an employer's facilities, for evaluating their median nerve condition and likelihood of developing carpal tunnel syndrome.

54 Claims, 13 Drawing Sheets

NERVE CONDITION MONITORING SYSTEM AND ELECTRODE SUPPORTING STRUCTURE

FIELD OF THE INVENTION

This invention relates to neurological monitoring. More particularly, this invention relates to monitoring of nerve conduction parameters. Still more particularly, this invention relates to a method and apparatus ("system") for monitoring carpal tunnel syndrome including monitoring conduction parameters of the median nerve.

BACKGROUND OF THE INVENTION

It has long been known that the conduction velocity of a nerve is affected by the health of a nerve. Disease affecting a nerve or injury to a nerve is generally accompanied by a decrease in nerve conduction velocity.

Carpel tunnel syndrome is a neuropathy of the median nerve occurring in the segment of the nerve which lies in the carpal tunnel within the underside of the wrist. This neuropathy ("sickness of the nerve") is associated with disease of or injury to the median nerve in the carpal tunnel. Carpal tunnel syndrome is becoming an increasingly significant health problem due to the changing demographics of the work population and the aggravation of this underlying biologic predisposition for the development of carpal tunnel syndrome by the stresses of the work environment. The incidence is rapidly increasing, and the costs associated with its treatment and with work-related disability are escalating. Because job-related activities are often a factor in carpal tunnel syndrome, it has become a major concern of employers, workers compensation insurers, and government agencies having jurisdiction over conditions in the workplace. At present, approximately half of all workers compensation claims are based on cumulative trauma disorders, also known as repetitive motion injuries. These injuries are predominantly carpal tunnel syndrome.

Despite the fact that carpal tunnel syndrome is a disease of insidious onset in which the nerve is progressively injured day by day, a patient typically does not seek medical attention until the condition has become sufficiently bothersome or painful as to interfere with normal activities. Unfortunately, by this time, the syndrome is often far enough advanced that surgery is the only effective treatment. Frequently after surgery, the patient cannot return to normal repetitive activities without risk of recurrence or complications.

Others have used nerve conduction velocity measurement to assist in diagnosing carpal tunnel syndrome in patients presenting with symptoms consistent with this condition. However, such prior art measurement systems suffer from a number of drawbacks rendering them unsuited to screening of an asymptomatic individual for the likelihood of developing carpal tunnel syndrome, which would permit safe and inexpensive prophylactic measures to avoid or mitigate the syndrome. Currently the measurement is performed using expensive, multi-purpose equipment, by testing personnel who are highly skilled in electrophysiology. The test may be made by applying a stimulating electrical pulse to the patient's skin, such as on the arm, and recording the distally occurring electrical signal, which has been propagated down the nerve in response to the stimulus pulse, such as at the patient's hand or fingers. The tester first attaches stimulating and pickup electrodes to the patient, generally by taping the electrodes to the patient's skin or perhaps surrounding the patient's finger(s) with nooselike wire electrodes. The electrodes are connected to a multi-purpose EMG machine, which generates electrical stimulating potentials and displays the action potential (also known as the depolarization curve) received by the pickup electrodes on a CRT or other display. The stimulating signal may be increased until an adequate number of nerve fibers are depolarized to produce a response waveform which is satisfactory in appearance to the tester. The tester then manually moves a cursor across the CRT screen to what appears to be the peak response of the action potential. The elapsed time between the stimulus and a maximal point on the response waveform is expressed in milliseconds. The tester measures the distance between the stimulus and pickup electrodes, and calculates the nerve conduction velocity by dividing the measured distance by the measured elapsed time.

The foregoing system generally allows variation of many parameters which should be controlled, and cannot be used in a cost-effective manner in the typical work environment. An on-the-job test is also subject to a range of environmental conditions which may be quite different from those in a neurologist's office, such as temperature variations which affect nerve conduction velocity and therefore interfere with interpretation of the test results.

The variable parameters in the prior art systems which ought to be controlled are generally the result of requiring a person, albeit a trained electrophysiologist, to set up and administer the test. For instance, the location and spacing of the electrodes and the visual selection of the maximal point of the response waveform on the CRT to determine the elapsed time are subject to inaccuracies, errors, and variations among testers. Moreover, the requirement of an in-office test by trained electrophysiologist using expensive, multipurpose equipment and the time-consuming nature of the prior art test render it expensive, and unlikely to be used as a screening technique due to the extensive time that the worker must be away from the workstation in order to complete the test. For these reasons, nerve conduction velocity tests have been used primarily as a means for confirming diagnosis of carpal tunnel syndrome rather than for prophylactic screening, treatment recommendation, and treatment monitoring.

Another drawback of prior art systems which have been used to monitor carpal tunnel nerve conduction velocity is the unavailability of an easily usable digital data output. For instance, certain known systems provide response waveform data as an image in a graphics file. This requires excessive data storage space, which is always undesirable but particularly so if the system is to be used to perform many tests in a remote field location. Moreover, it is difficult to extract pertinent data from a test result stored as an image, which renders comparison of results from different tests quite difficult.

It is therefore a general object of the invention to provide a neurological monitoring system which avoids the above-described drawbacks of the prior art.

It is a more specific object of the invention to provide a neurological monitoring system which is useful for prophylactic screening, treatment recommendation, and/or treatment monitoring in connection with carpal tunnel syndrome.

It is another object of the invention to provide a neurological monitoring system which does not require highly skilled personnel for effective use.

It is another object of the invention to provide a neurological monitoring system which may be easily used in a wide variety of locations, including work areas.

It is another object of the invention to provide a neurological monitoring system which reduces errors in the placement of electrodes and determination of the distance between them.

It is another object of the invention to provide a neurological monitoring system which reduces errors in the determination of elapsed time between stimulus and response.

It is another object of the invention to provide a neurological monitoring system in which response signals generated by sensory nerves may be used.

It is another object of the invention to provide a neurological monitoring system which facilitates storage of data relating to test circumstances as well as the test results.

It is another object of the invention to provide a neurological monitoring system which facilitates correlation of data from different tests.

Finally, it is an object of the invention to provide such a neurological monitoring system which is simple, rugged, reliable, and inexpensive.

In accordance with the foregoing objects, the neurological monitoring system of the present invention comprises a portable, substantially automatic nerve conduction velocity monitoring system. The monitoring system includes stimulating and pickup electrodes disposed in a fixed relationship to one another, adapted to contact skin areas on the forearm and hand, respectively, adjacent nerves passing through the carpal tunnel. The monitoring system further includes means for applying stimulus electrical signals to the stimulating electrodes, and means for processing and storing data relating to the electrical signals received at the pickup electrodes.

Other objects and features of the invention will become apparent to those skilled in the art in view of the following specification and claims and the drawings.

DETAILED DESCRIPTION OF THE PREFERRED EMBODIMENT

Figure 1:
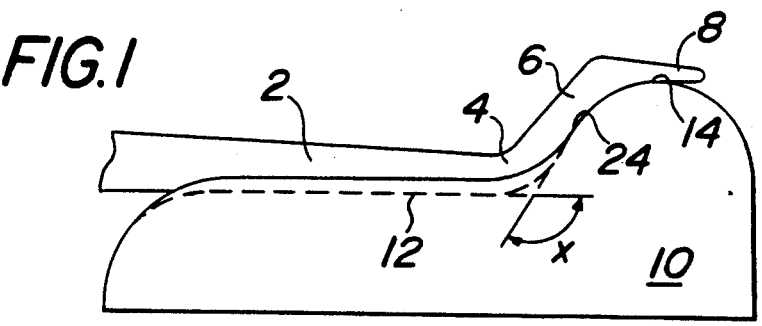
FIGS. 1 and 2 are elevations of the system of the invention, illustrating the preferred electrode-supporting structure.

FIG. 1 is an elevation of the system of the present invention, illustrating certain mechanical aspects thereof, and in particular, the manner in which it interfaces with the arm of a patient being tested. As has been described, in the prior art stimulus and response electrode sets are individually applied to a patient, such as by taping. The present invention avoids the requirement of a trained electrophysiologist to position the electrodes with respect to the patient and measure the interelectrode spacing, by providing an electrode supporting structure 10 having electrodes mounted to it at predetermined locations. Because this electrode supporting structure also serves as a housing for monitoring circuitry in the preferred embodiment, it will be referred to as housing 10. Preferably and as shown, the outer surface of the housing 10 includes arm and hand supporting surfaces shaped to provide accurate, reliable, repeatable, and easy positioning of electrodes with respect to the patient. This feature of the invention is most easily seen by viewing FIG. 1 together with FIG. 2, which is an elevation of the housing 10 of FIG. 1 as viewed from the left of FIG. 1.

Figure 2:
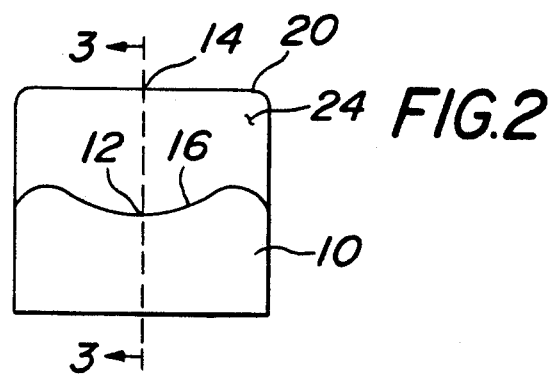

The testing system includes electrodes mounted to the housing 10 at location 12 and adapted to contact the forearm 2 of the patient, and electrodes mounted to housing 10 at location 14 and adapted to contact a finger 8 of the patient. While a variety of housing shapes and electrode mounting locations might undoubtedly be used, the preferred electrode supporting housing of the present invention has several features which facilitate the accurate and reliable positioning of the patient's arm and hand with respect to the electrodes. As shown in FIG. 2, electrode mounting location 12 is on the curved surface 16 of the housing and adapted to conform to a human forearm, generally having the shape of a portion of a cylindrical surface. The concave shape of surface 16 tends to center and properly laterally position the forearm 2 with respect to the housing 10 and electrodes. The housing 10 also includes means for properly positioning the forearm and hand longitudinally with respect to the housing 10. The preferred embodiment, shown in FIGS. 1 and 2, includes a second surface 24 adapted to contact the patient's hand when the patient's forearm 2 is properly positioned with respect to surface 16. Surface 24 is longitudinally angled with respect to the surface 16 receiving the forearm 2. The angle X between the surfaces is desirably about 135°, but other angles between 90° and 180° may also be used. Accordingly, when the forearm and hand of the patient are properly positioned, the patient's wrist 4 is bent upwardly and the patient's palm 6 is pressed against surface 24, thereby limiting longitudinal motion of the patient's forearm and hand with respect to the housing and electrodes. In the preferred embodiment, the patient's fingers 8 are disposed on a separate surface 20 which includes electrode mounting location 14. While the arrangement shown in FIGS. 1 and 2 is preferred for maintaining the electrodes and the patient's arm properly positioned with respect to each other, other means such as means abutting the finger tips or the palm between bases of fingers might also be employed.

It is noted that the pickup electrodes are mounted to housing 10 in location 14 so as to contact the patient's finger 8 and receive signals from the digital nerves. This permits monitoring of the nerve conduction velocity in the sensory nerves, which is preferred. In contrast, typical prior art systems respond to muscle depolarization signals, such as in muscles in the palm, which provides a larger signal but a nerve conduction velocity measurement which is a less sensitive indication of median nerve condition.

Figure 3:
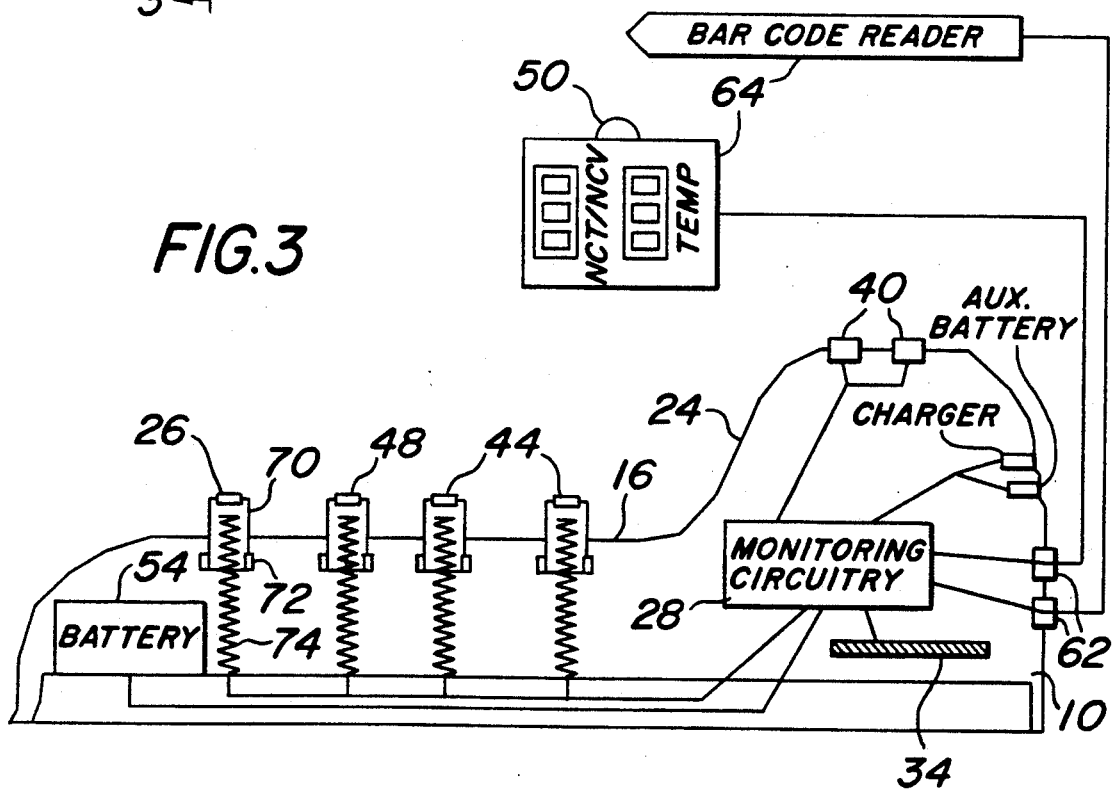
FIG. 3 is a schematic cross-section of the preferred electrode-supporting structure of the invention, taken along the lines 3—3 in FIG. 2.

FIG. 3 shows a schematic cross-section of the electrode mounting housing of the invention, taken along the line 3—3 in FIG. 2. FIG. 3 illustrates certain features of the preferred embodiment of the invention such as electrodes and input/output devices which, for convenience, are not shown in FIGS. 1 and 2.

The pickup electrodes comprise a pair of electrodes 40, mounted to the surface 20 of housing 10 and adapted to contact the patient's contacting finger 8 when the apparatus is in use. Electrodes 40 may comprise snaps adapted to receive disposable, pre-gelled electrodes, such as are in use in the art. Electrodes 40 may be rigidly affixed to housing 10.

The stimulating electrodes comprise a pair of electrodes 44 which are disposed so as to be in contact with a patient's forearm 2 when the apparatus is in use. Stimulating electrodes 44 and pickup electrodes 40 are located so that the patient's wrist 4, and thus the carpal tunnel, is located between stimulating electrodes 44 and pickup electrodes 40 when the apparatus is in use. A ground electrode 26 is also provided, which likewise contacts the forearm 2 of the patient and provides a ground reference for the measurement.

In accordance with an important object of the invention, a temperature sensor 48 is also provided, which is mounted to housing 10 so as to contact the patient's skin during testing, preferably the patient's forearm 2. Sensing of the patient's temperature, particularly in the vicinity of the carpal tunnel, permits the monitoring system to measure and account for the effects of temperature on nerve conduction velocity. Nerve conduction velocity is known to be a strong function of temperature, which may vary from patient to patient and from time to time, particularly when monitoring is performed in an uncontrolled environment such as a workplace which may be very hot or very cold.

Whereas the pickup electrodes 40 may be fixed to housing 10 and still provide adequate contact to the patient's finger 8 under normal circumstances, this is not necessarily the case for electrodes 26 and 44 and temperature sensor 48. These forearm-contacting devices must be able to accommodate forearms differing widely in size, resilience, and the like. Accordingly, in the preferred embodiment of the invention, electrodes 26 and 44 and temperature sensor 48 are not rigidly affixed to housing 10, but rather are spring loaded. As shown with respect to ground electrode 26, in the preferred embodiment the electrode structure comprises a piston-like upper portion 70 which is biased upwardly by a spring 74. Upper portion 70 is provided with a snap for fastening a pre-gelled electrode. Annular projection 72 captures upper portion 70 within the housing 10. This arrangement permits the electrode to move up and down in a piston-like manner to adjust to the patient's forearm, but avoids lateral movement which might introduce errors into the measurement. Electrodes 44 and temperature sensor 48 are also similarly structured for resilient mounting to housing. Of course, equivalent means for mounting the electrodes and sensors may be employed to ensure adequate contact with the patient's forearm during measurement.

Desirably, the electrode-supporting structure also provides a housing for at least a substantial portion of the monitoring and ancillary circuitry required, so that the apparatus is substantially self-contained for ease of transport and use. Accordingly, as shown in FIG. 3, the housing 10 houses monitoring circuitry 28, a removable memory device 34 for storage of test results and other information, and a battery 54 to enable safe and portable operation of the system. Discussion of other aspects of the system of FIG. 3 will be deferred until operation of the system has been described.

Figure 4:
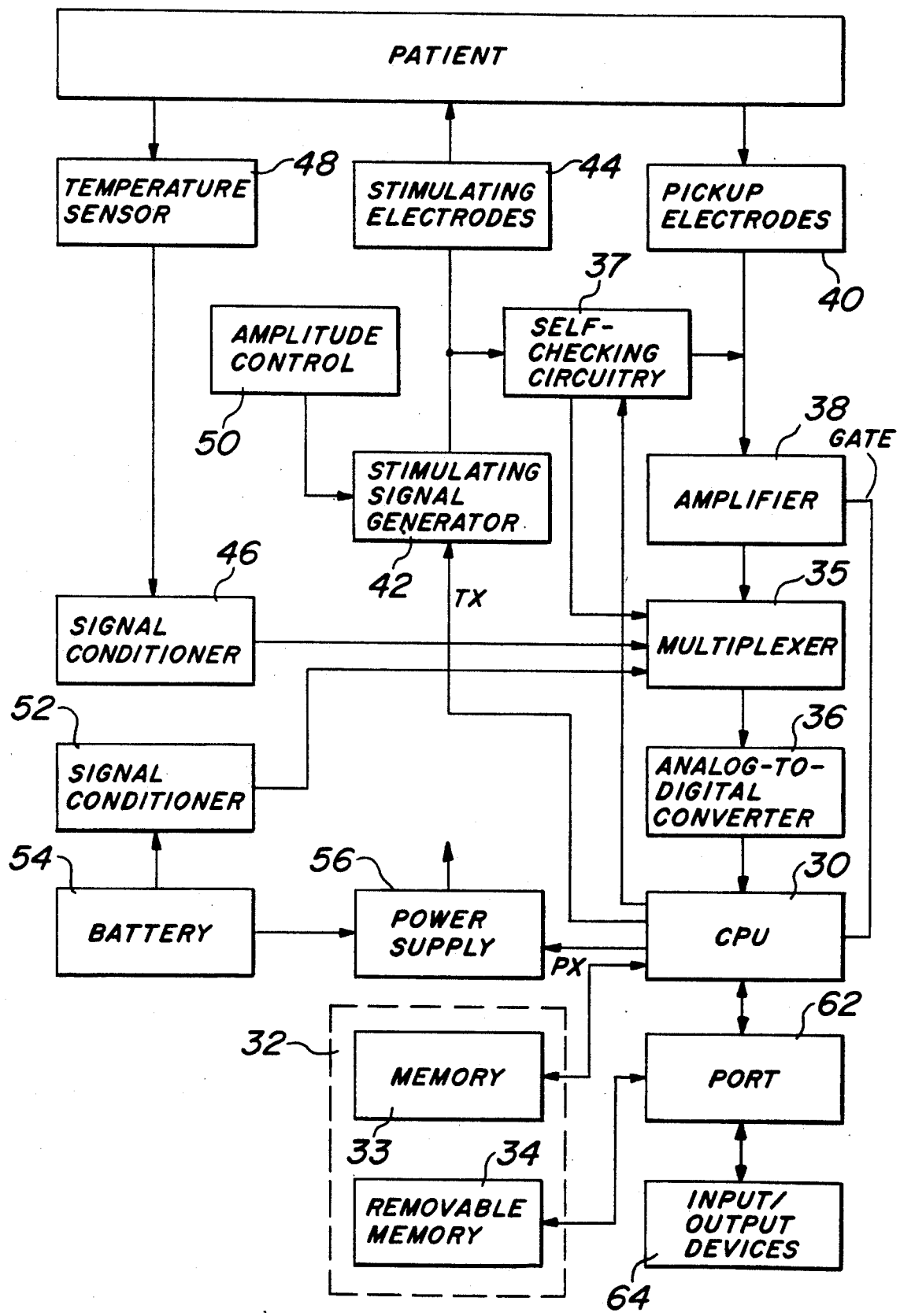
FIG. 4 is a block diagram of the preferred circuitry of the present invention.

FIG. 4 is a block diagram illustrating the general features of the preferred monitoring apparatus of the present invention. System power is provided by battery 54. A power supply 56 coupled to battery 54 generates and/or regulates such potentials as are needed for operation of the remaining circuitry of the system.

The basic elements of a nerve condition monitoring system include a stimulating signal generator coupled to the stimulating electrodes for generating electrical stimulating signals capable of stimulating neurological activity, and a response signal processor coupled to the pickup electrodes for processing neurological response signals received at the pickup electrodes in response to the application of a stimulating signal to the patient. For nerve conduction velocity monitoring, the response signal processor determines the elapsed time between application of a stimulating signal and the receipt of a response signal by the pickup electrodes having a predetermined characteristic, which characteristic is selected to correspond to a neurologically significant event. In the preferred embodiment illustrated in FIG. 4, the response signal processor includes amplifier 38, A/D converter 36, and CPU 30 operating under control of programs stored in memory 32. This structure is preferred since it enables CPU 30 to also provide the functions of controlling the overall operation of the monitoring system, computation of test results, storage and manipulation of data, and communication with various input/output devices. However, other response signal processors performing the necessary functions may also be used. A multiplexer 35 is included to enable A/D conversion and digital processing of other analog signals generated in the apparatus.

The monitoring system operates under control of central processing unit ("CPU") 30, in accordance with programs stored in memory 32. Memory 32 may also store data generated during nerve condition monitoring. Desirably, memory 32 includes a removable static memory 34 to enable nerve condition monitoring data to be delivered in a tangible medium to a desired location, but other data transmission means may also be used. Memory 32 also includes non-removable memory 33, which may include RAM and EPROM.

Stimulating electrodes 44 are coupled to a stimulating signal generator 42, which supplies electrical signals sufficient to stimulate neurological activity in the patient and produce a detectable response at pickup electrodes 40. The generation of stimulating signals by generator 42 is controlled by CPU 30. Such stimulating signals are preferably pulses. The amplitude of the stimulating signals generated by generator 42 may be controlled by the tester using amplitude control 50, or may alternatively be automatically controlled by CPU 30.

The analog response signal received at pickup electrodes 40 is typically far too small to be directly detected, and so it is amplified to detectable level by amplifier 38. The analog output signal from amplifier 38 is supplied by multiplexer 35 to the input of analog to digital ("A/D") converter 36, which generates digital signals related to its analog input and supplies such digital signals to CPU 30. Desirably, the signal received at pickup electrodes 40 is filtered prior to analysis to eliminate spurious signal components; such filtration may desirably be included in amplifier 38. The digitized response signal received by CPU 30 is preferably stored in memory 32 and is also preferably analyzed by CPU 30 to determine the occurrence of a predetermined response signal condition, such as the peak of the response, in accordance with a stored program. Since the stimulating signal is generated under control of CPU 30, the elapsed time between the stimulus and the occurrence of the predetermined response event may be determined by the system. Further, since the distance between stimulating electrodes 44 and pickup electrodes 40 is fixed, and data representing the interelectrode spacing may be stored in memory 32, the nerve conduction velocity may be computed in CPU 30 in accordance with the elapsed time and the interelectrode distance.

The system of FIG. 4 also includes a temperature sensor 48 coupled to a signal conditioning circuit 46, such as may be required to amplify or otherwise process the output of temperature sensor 48 prior to its input to A/D converter 36. The conditioned analog temperature signal is supplied by multiplexer 35 to the input of A/D converter 36, where it is converted to digital form and coupled to CPU 30. Such a digital temperature signal may be used in CPU 30 in normalizing or otherwise accounting for temperature effect on nerve conduction velocity measurement.

The system of FIG. 4 also includes a signal conditioner 52, which receives the battery voltage from battery 54 and provides an output signal which is related to the battery voltage. This output signal is supplied by multiplexer 35 to an input of A/D converter 36. This enables CPU 30 to analyze the condition of the battery 54 so as to be able to indicate the need for recharging or replacement, or the like.

The system of FIG. 4 includes one or more input/output (I/O) devices 64 coupled to CPU 30 by one or more ports 62. Such devices 64 may be used for input and/or output of information to and/or from CPU 30. In the preferred embodiment, the system includes a bar code reader as an input device, which may be used to scan bar coded information to easily input such information to the system. Output devices may include indicators, alphanumeric displays such as LED or LCD displays, and audio output devices. Alphanumeric outputs may provide output information relating to monitoring results, as well as user prompts to assist the user in operating the system.

As briefly described above, the system of FIG. 4 includes a removable static memory device 34, which in the preferred embodiment is a RAM card but may also comprise other conventional removable storage media such as disks. Removable memory 34 may store data relating to the patient being tested, such as identifying information (e.g. social security number) and other data such as the patient's name, age, occupation, employer, and the like. It may further contain stored data relating to the test circumstances, such as the date and time of test, the serial number of the apparatus performing the test, and a unique identifying number for the test. It may further contain data relating to the results of the test, such as the temperature which was measured and the elapsed time or nerve conduction velocity determined. It is preferred also to store data in memory 34 representing the actual response waveform which was received at pickup electrodes 40, particularly in a format which permits easy manipulation or analysis of the data, such as periodically sampled response signal amplitude data. This enables subsequent confirmation of the elapsed time and nerve conduction velocity which were determined in the test. Moreover, it is believed by applicants that other attributes of the received signal may be correlated with the condition of the nerve being monitored. Storage of waveform-related data enables establishing such correlation and analysis of nerve condition based on the waveform attributes. Significantly, in the present invention this waveform data is quickly and easily obtained, in a form well suited to further analysis, by persons who need not be trained in electrophysiology. The waveform and other data stored in removable memory 34 may later be provided to a neurologist for analysis.

Removable memory device 34 may further contain program information; operating programs and other information may be downloaded into memory 33 from removable memory 34. This would facilitate, for instance, updating of operating programs to be used. It should be noted that the preferred circuitry shown in FIG. 6 does not permit such operation.

The system of FIG. 4 includes self-checking circuitry 37, operable under control of CPU 30. This circuitry generates a simulated response signal from the stimulating signal, and couples it to the response signal processor. Evaluation of the processed simulated response signal enables calibration and/or determination of whether a large portion of the system is properly functioning.

Finally, in the system of FIG. 4, CPU 30 controls operation of amplifier 38 and of power supply 56. Although the modes of such control will be described in detail below, they are briefly described as follows. In order to prevent adverse effects on the measurement due to spurious artifacts which typically occur shortly after application of a stimulating signal, the system includes means for inhibiting amplifier response to such spurious signals. CPU 30 inactivates amplifier 38 for a time after initiating the stimulating signal. By preventing amplifier 38 from responding to such spurious signals, the quality of signal which is output by amplifier 38 is substantially improved. CPU 30 also controls operation of power supply 56, to reduce power consumption when the system is operating in modes which do not require all circuitry to be fully powered. This helps to conserve battery power, which is an important consideration in portable equipment.

FIGS. 5-11 are schematic diagrams of the circuitry of the preferred monitoring apparatus of the present invention. As the elements of this circuitry are largely conventional, and it is believed that their mode of operation will be generally apparent to persons skilled in the art upon review of the drawings, the following descriptions will generally be brief.

Figure 5:
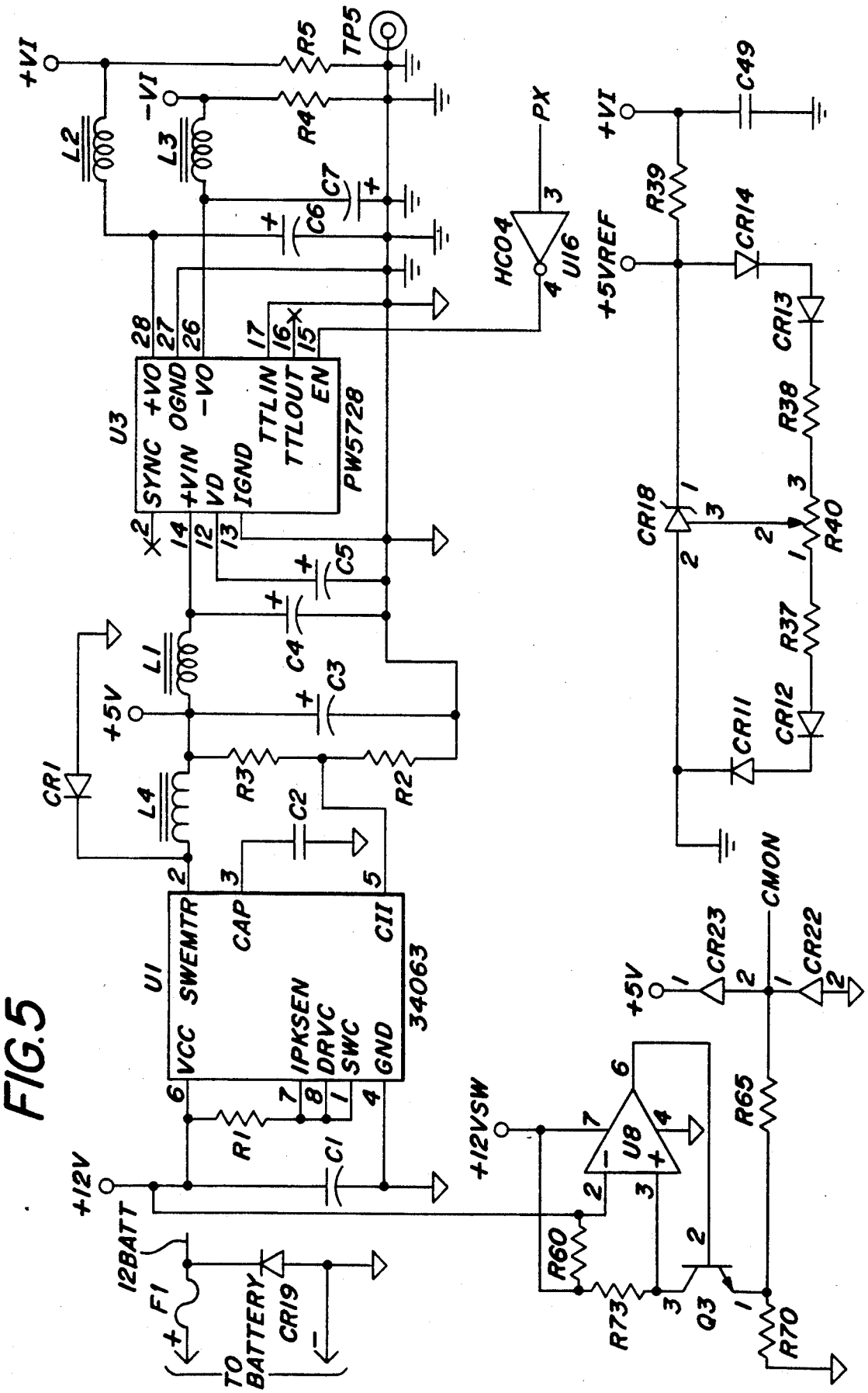
FIG. 5 is a schematic diagram of the power supply of the preferred embodiment.

FIG. 5 shows the preferred power supply 56 of the present invention. The battery 54 is coupled through fuse F1 to provide a protected supply 12BATT. This supply is protected against reverse polarity connection by diode CR19. 12BATT is connected to the supply potential designated +12VSW through the switch portion of switch/potentiometer R48, shown in FIG. 10. Actuation of the switch applies power to the system, and may cause the microprocessor to initialize its peripherals, execute self-checking routines, and the like, as determined by its stored program. By using a ganged switch and potentiometer R48, with the potentiometer used to control stimulating signal amplitude, the system is provided with a single control to facilitate ease of training and use.

The switched battery supply potential +12VSW is coupled to the main circuit supply potential +12V through current sensing resistor R60. The voltage across R60 is processed by an amplifier circuit including U8 and Q3 to generate a current-related voltage signal CMON, which is coupled to the ADC3 input of U5 to enable the system to monitor its current consumption.

A DC to DC converter circuit based on DC to DC converter control circuit U1 generates a regulated potential +5V from the +12V supply. DC to DC converter U3 generates a bipolar supply having output potentials +V1 and −V1 with respect to ground, which are used to supply the amplifier circuits described herein. Since operation of the amplifiers may waste considerable power if they are not actively processing useful signals, operation of U3 is controlled by microprocessor U5 through line PX. Also shown in FIG. 5 is a reference generating circuit based on CR18 which generates a high quality reference voltage +5VREF from +V1, which is supplied to U5.

Figure 6A:
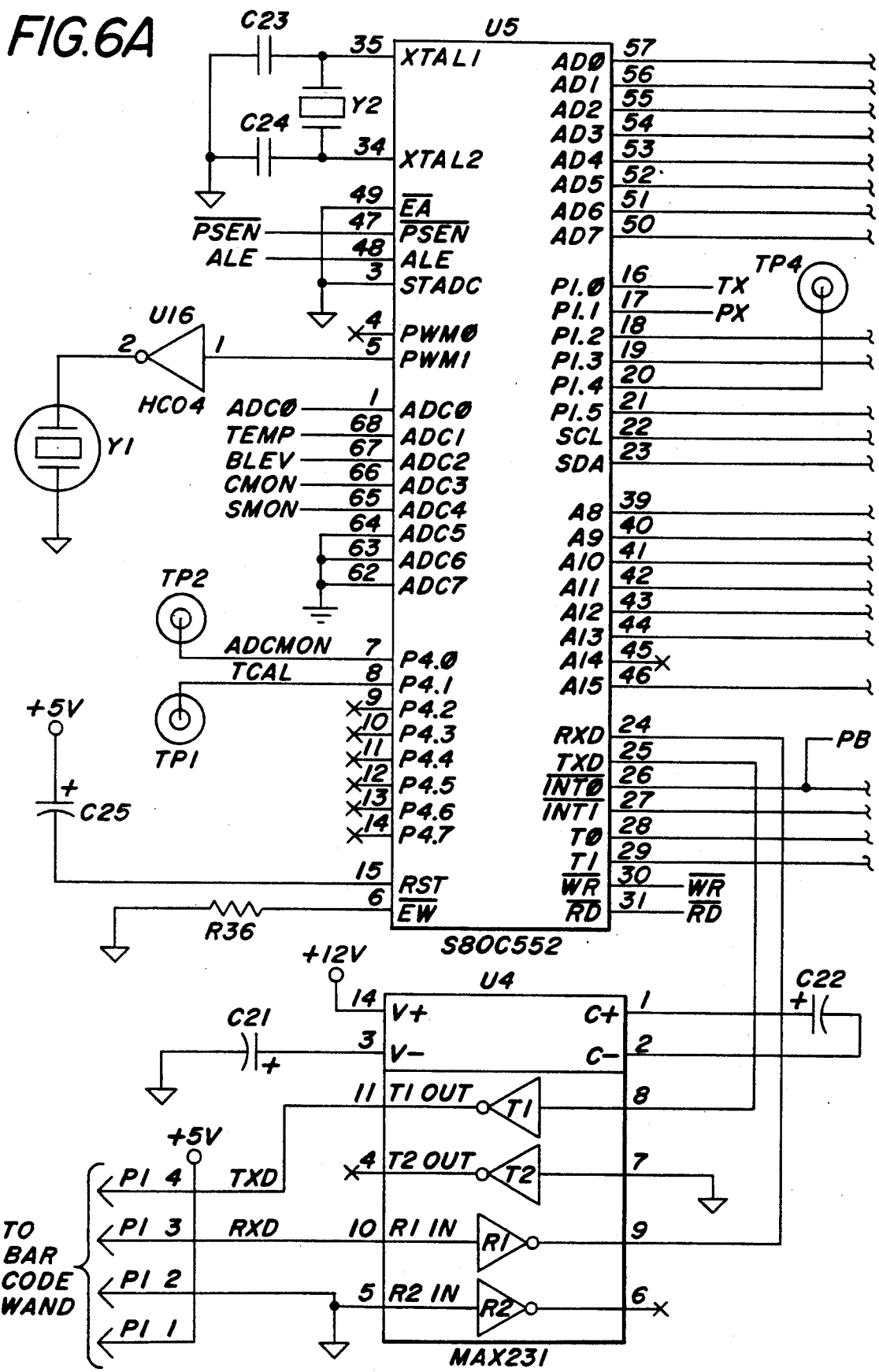
FIGS. 6A, 6B and 6C are schematic diagram including the CPU, memory and A/D converter of the preferred embodiment.
Figure 6B:
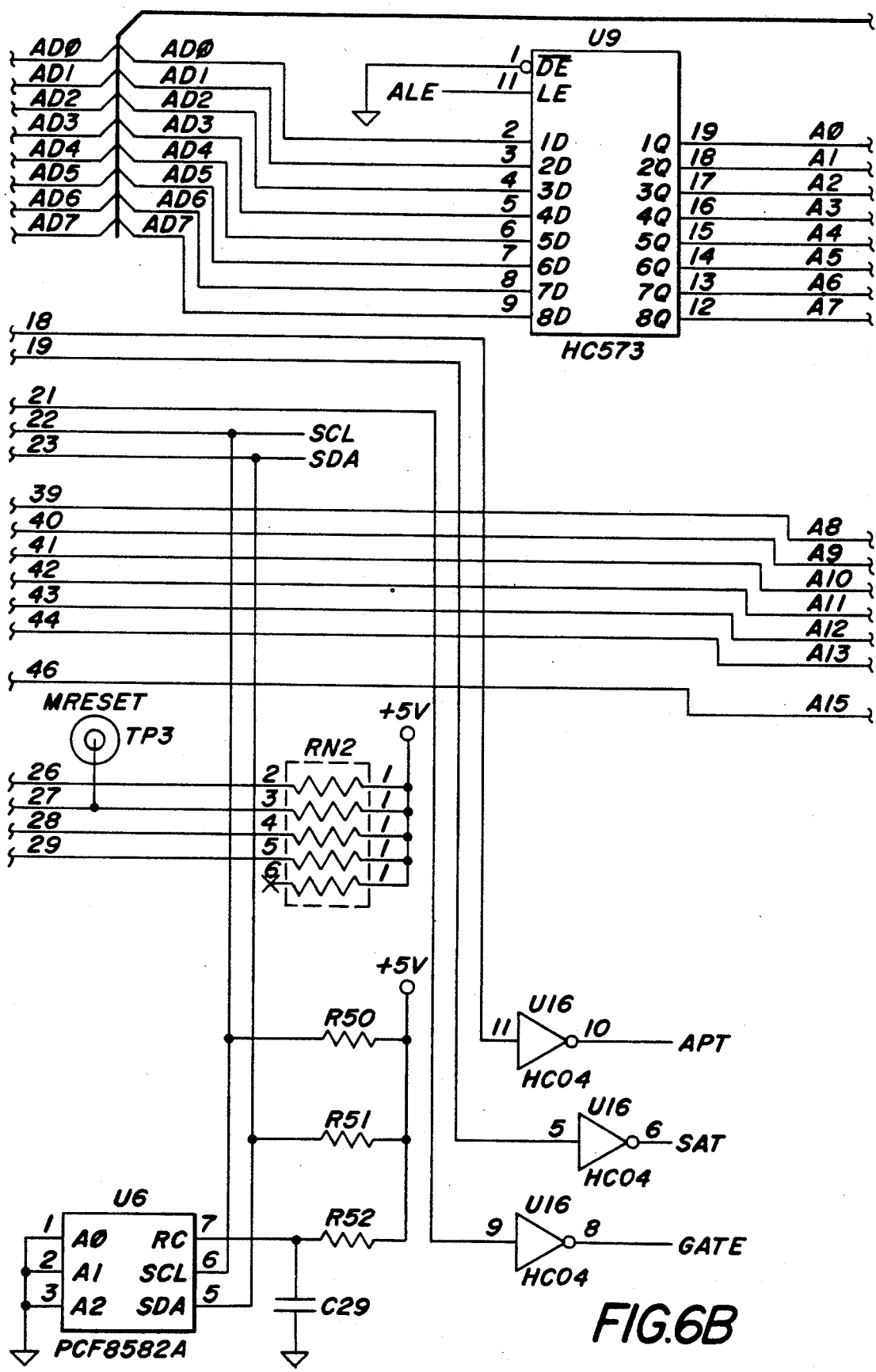
Figure 6C:
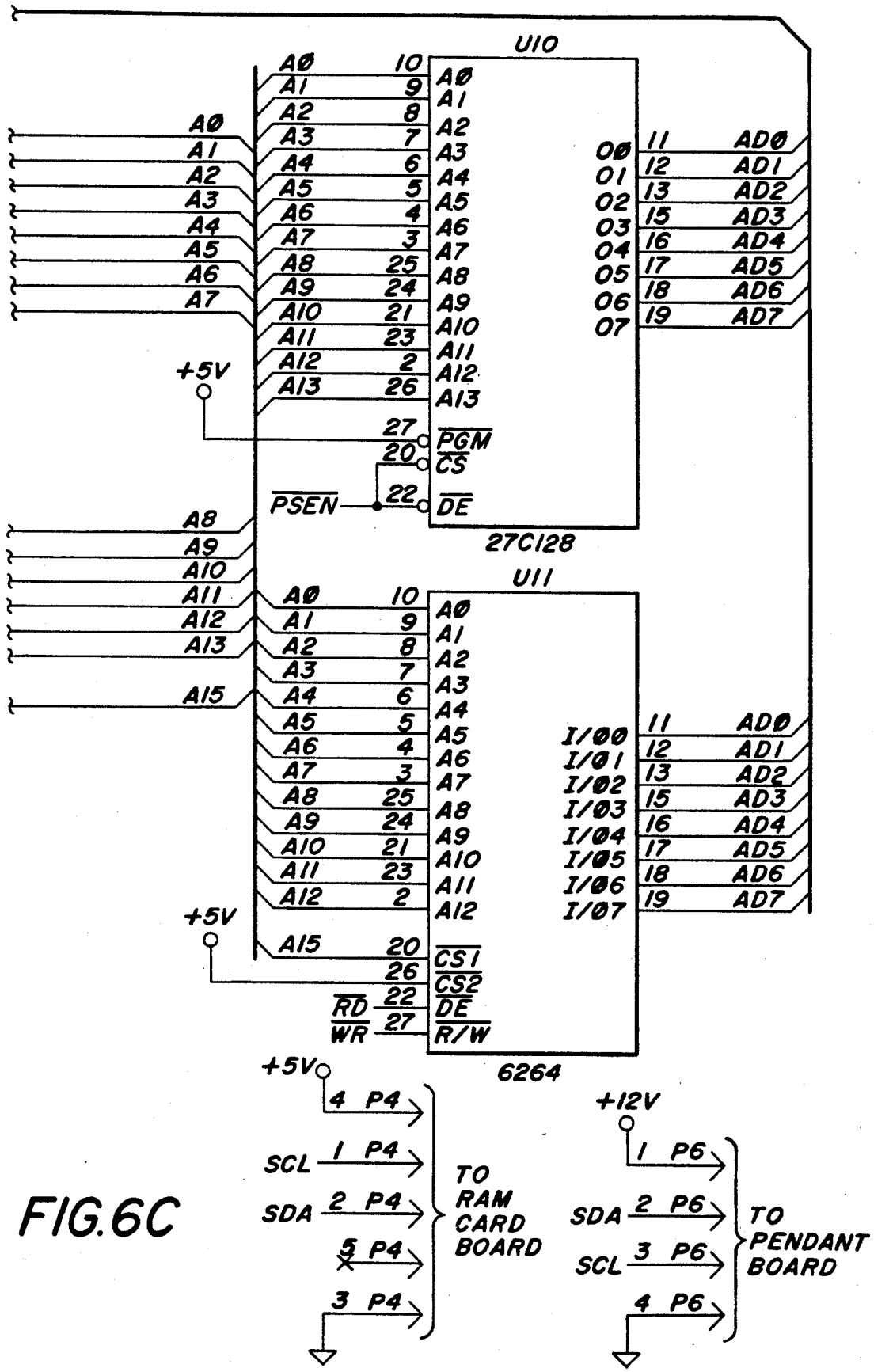

FIGS. 6A, 6B and 6C are a schematic diagram of circuitry including CPU 30, memory 33, multiplexer 35, and A/D converter 36. A microprocessor, type S80C552, provides a CPU, an A/D converter, and an eight channel multiplexer having inputs ADC0 through ADC7, five of which are used in the present system. U5 also contains clock generating circuitry which generates appropriate clock signals in conjunction with crystal Y2. Memory 33 comprises EPROM U10 and RAM U11 which are operated under control of address latch U9, and EEPROM U6 which stores sequential numbers indicating the number of tests which have been performed by the system. U11 as shown is an 8K×8 SRAM.

Microprocessor U5 includes various input and output lines which are used to interface with various input/output and memory devices, some of which are discussed in connection with other figures. Certain of the ports 62 illustrated in FIG. 4 are implemented by such microprocessor input and output lines. An output PWM1 is used to drive an audio output device Y1. Lines SCL and SDA provide a high-speed interchip communication bus, which is used to control both alphanumeric and indicator display outputs and to communicate with removable memory device 34. Lines P1.2 and P1.3 are used to control a self-test circuit comprising U7. Also, U5 is coupled to line TX to control stimulating signal generator 42, line PX to control power supply 56, and line GATE to control amplifier 38.

FIG. 6A also shows a general-purpose input/output port comprising U4, an RS-232 driver/receiver which communicates with microprocessor U5 over lines RXD and TXD. U4 converts RS-232 signal levels from an external device to TTL levels usable by U5, and converts TTL level signals generated by U5 to RS-232 levels for use by an external device. The preferred input device of the present invention is a bar code reader, which may be coupled to the RS-232 port provided. Such a device permits simple and reliable data input to the monitoring system by personnel with minimal training. The apparatus may also communicate with other computers via the RS-232 port.

Figure 7:
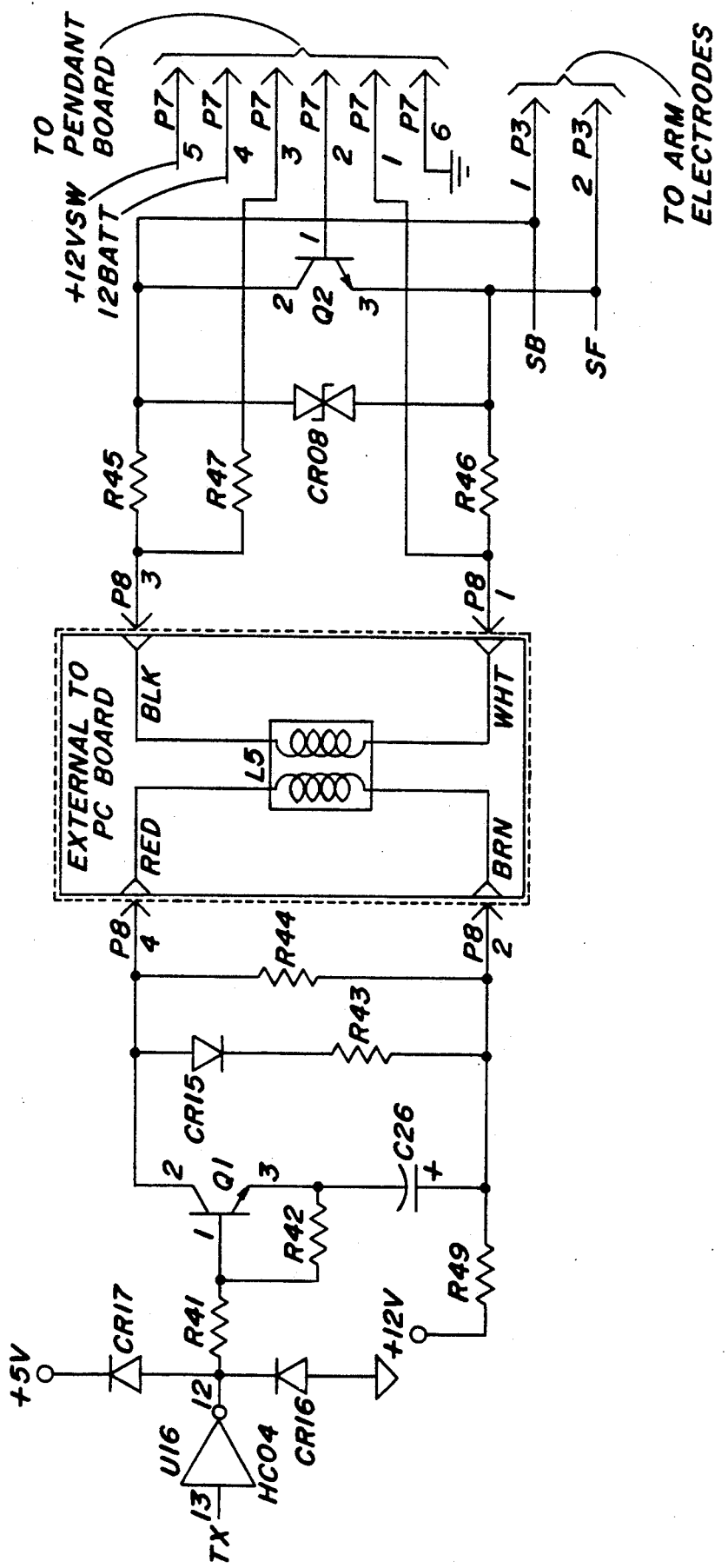
FIG. 7 is a schematic diagram of stimulating signal generation and control circuitry of the preferred embodiment.

FIG. 7 is a schematic diagram including stimulating signal generator 42. Generator 42 operates under control of microprocessor U5 via line TX. When line TX is high, capacitor C26 is charged; when TX goes low, transistor Q1 is turned on, dumping capacitor C26 into the primary winding of step up transformer L5. This causes a large pulse to appear across the secondary of L5. Generator 42 includes means for controlling the characteristics of the stimulating signals generated. The secondary pulse is coupled to stimulating electrodes 44 through a pulse amplitude control circuit based on transistor Q2. The pulse amplitude control circuit provides a variable load on the secondary of transformer L5 in accordance with the setting of potentiometer R48, comprising amplitude control 50 of FIGS. 3 and 4. Switch/potentiometer R48 is desirably included in a handheld display and control device connected to the housing 10 by a flexible cable, as shown in FIG. 3. Accordingly, R48 is shown in FIG. 10.

Figure 8A:
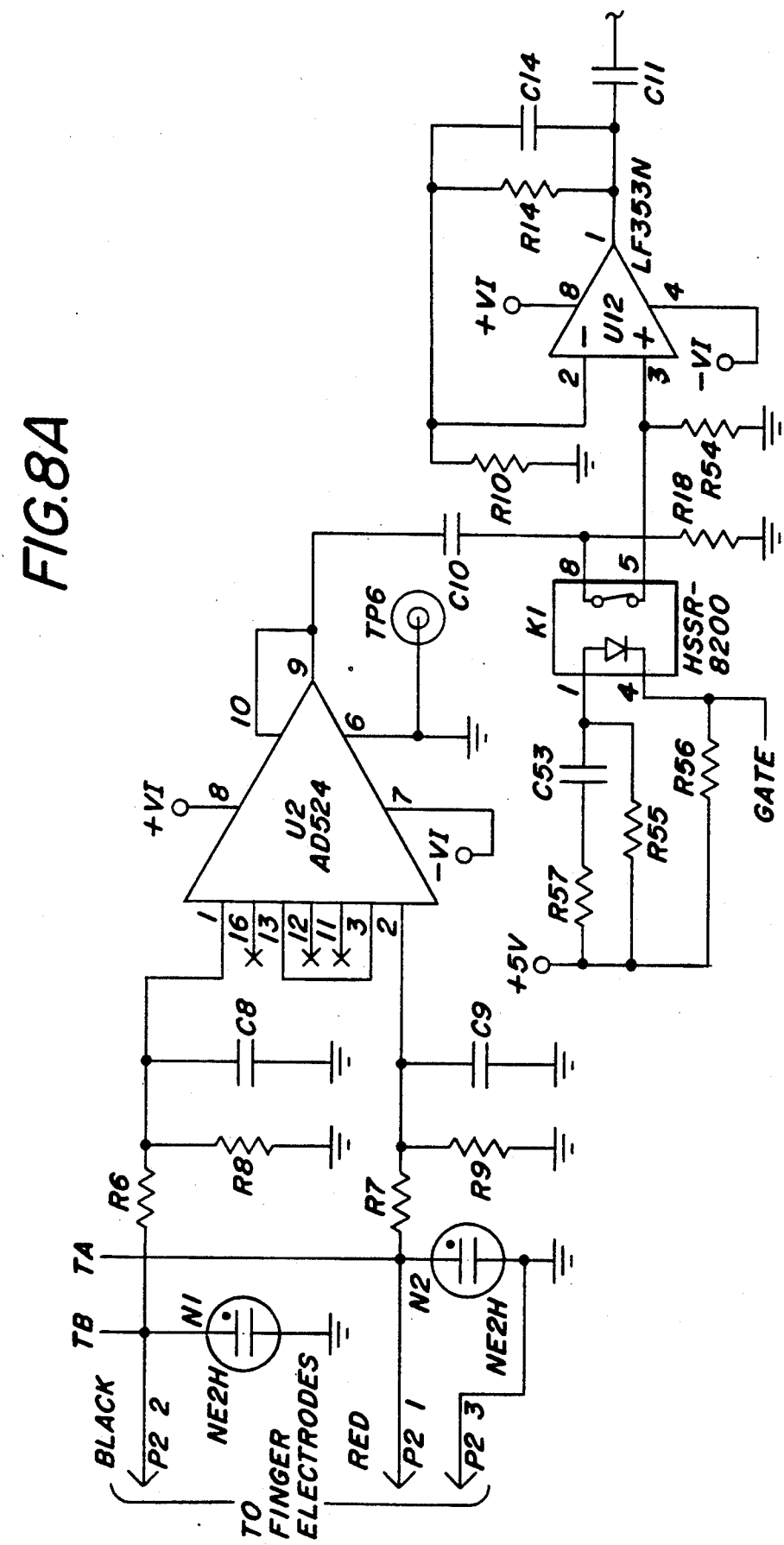
FIGS. 8A and 8B are a schematic diagram of the response signal amplifier of the preferred embodiment.
Figure 8B:
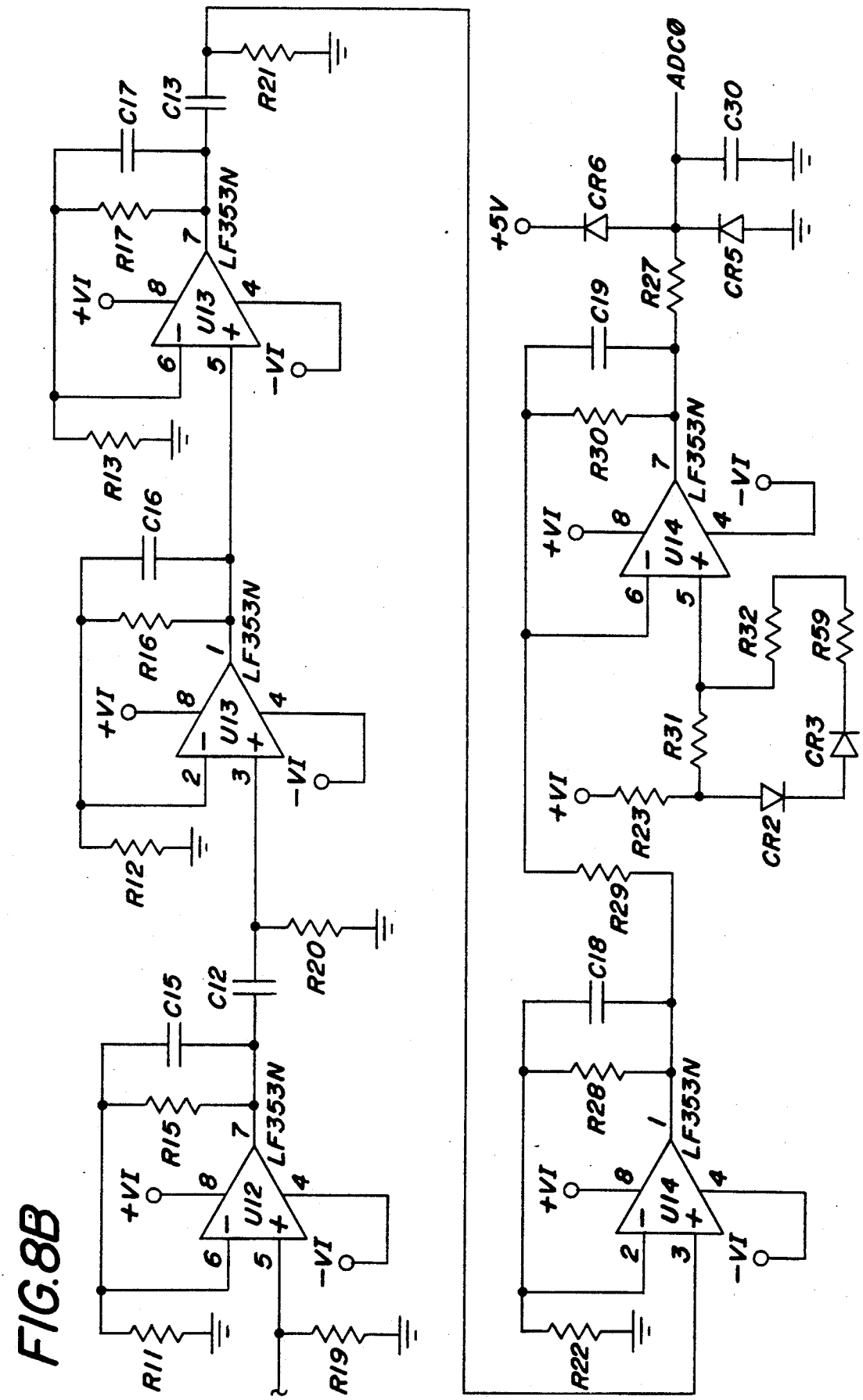

FIGS. 8A and 8B are a schematic of the preferred circuit of amplifier 38 of the present invention. Amplifier 38 is a gated multistage bandpass amplifier.

The first stage of the amplifier circuit is based on U2, a type AD524 instrumentation amplifier. Each of a pair of inputs of U2 is coupled to one of the pickup electrodes 40. The inputs are protected by gas discharge devices N1 and N2, and by attenuators comprising R5-R9 which maintain the limited electrode voltage within the input range of U2. The output of U2 is coupled through capacitor C10 and a switch to the input of a six stage amplifier comprising U12, U13, and U14. This amplifier is a bandpass amplifier, having a center frequency of about 650 Hz and a passband of about ±350 Hz. The center frequency gain of circuit is about 200,000. Because of the large gain of the bandpass amplifier, large spurious differential input signals at electrodes 40 can have adverse effects on the amplifier output. Such adverse effects may be caused by saturation of the amplifier components, as well as charging of capacitors. As the amplifier components come out of saturation or the capacitors discharge, substantial spurious components may appear in the amplifier output waveform. Such effects may be tolerable to a degree in prior art systems, since a trained electrophysiologist may be able to adequately determine a desired waveform feature by visual inspection of a graphic output. However, such effects are highly undesirable in the environment for which the present invention is primarily intended, namely substantially automated monitoring including nerve conduction velocity measurement in a wide variety of locations by personnel who are not necessarily trained electrophysiologists. Accordingly, in accordance with an important aspect of the invention, amplifier U2 is disconnected from the input of the multistage amplifier at by a switch comprising optoisolator K1. This switch is operated under control of microprocessor U5, through the GATE line. At about the time when U5 outputs a control signal TX to cause generation of a pulse, it outputs a high signal to the GATE line, which causes the LED of optoisolator K1 to be off and the phototransistor switch of K1 to be open, thus disconnecting the output of U2 from the input of U12. This condition is maintained until a sufficient time (e.g. 0.25 milliseconds) has passed that the spurious signals, such as may be produced by skin surface conduction, would likely have decayed. After such a time interval, microprocessor U5 drives the GATE line low, causing current flow in the LED of K1 and thus conduction of the phototransistor switch of K1, thereby coupling the output of U2 to the input of U12. While this switching scheme is preferred, other types of switching circuitry may no doubt be employed to prevent amplifier response to spurious response waveform components. The output of the multistage amplifier circuit is designated ADC0 and is applied to the similarly-designated multiplexer input to the A/D converter of U5.

Figure 9:
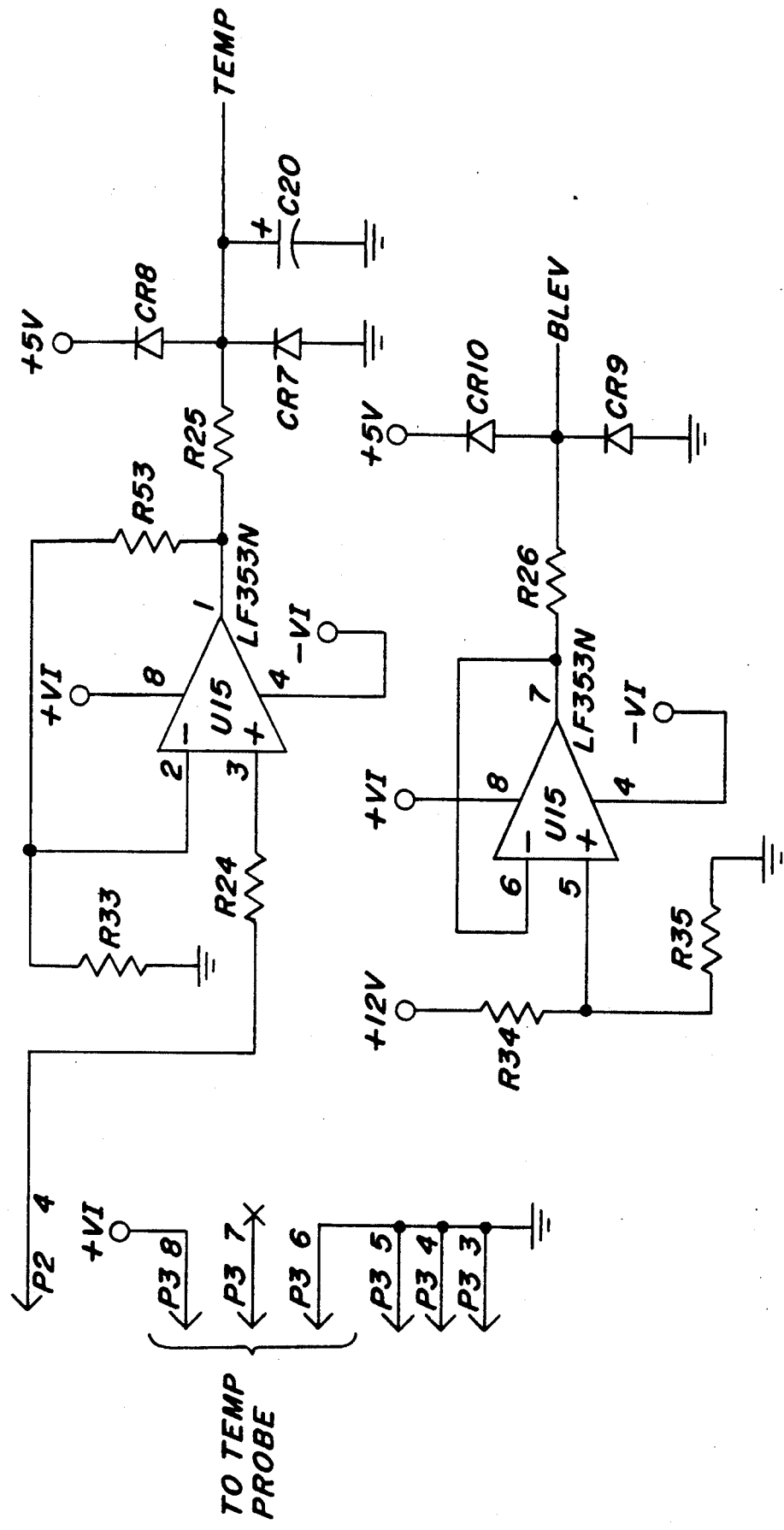
FIG. 9 is a schematic diagram of temperature and battery voltage signal conditioning circuits of the preferred embodiment.

FIG. 9 shows schematic diagrams of signal conditioning circuits 46 and 52 which are used in connection with providing temperature and battery voltage signals. A temperature sensor 48, such as a type LM35 temperature sensor, is coupled to an amplifier comprising U15. The TEMP output of this circuit is coupled to the ADC1 multiplexer input coupled to the A/D converter of U5.

A second amplifier comprising U15 has an input coupled to the voltage +12V through an attenuator. The output of this circuit, BLEV, is coupled to the ADC2 input of the multiplexer coupled to the A/D converter of U5. This circuit monitors the battery voltage, enabling microprocessor U5 to take appropriate action such as indicating a low battery condition or preventing system operation if the battery voltage is insufficient.

Figure 10A:
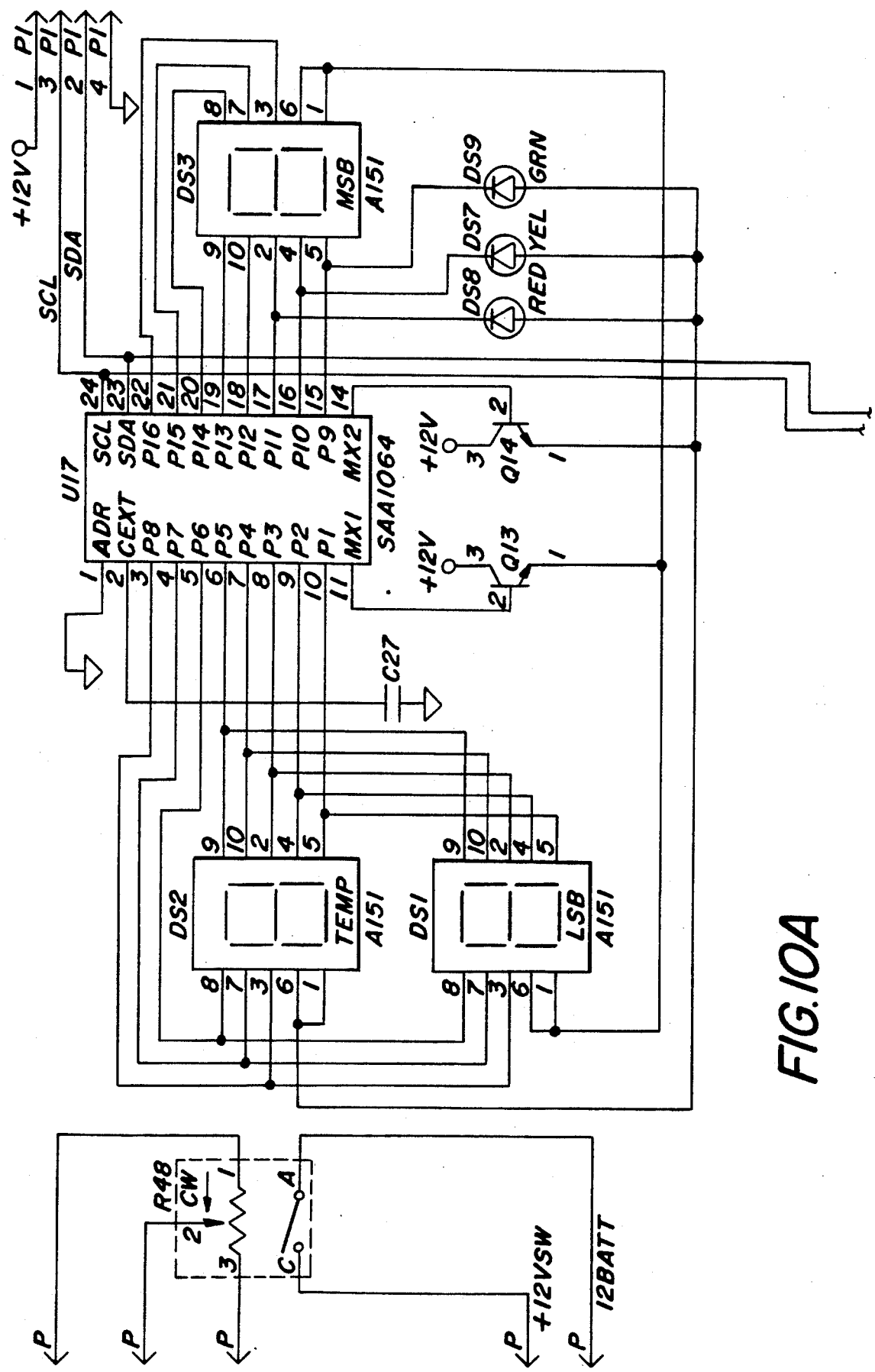
FIGS. 10A and 10B are a schematic diagram including input/output circuitry of the preferred embodiment.
Figure 10B:
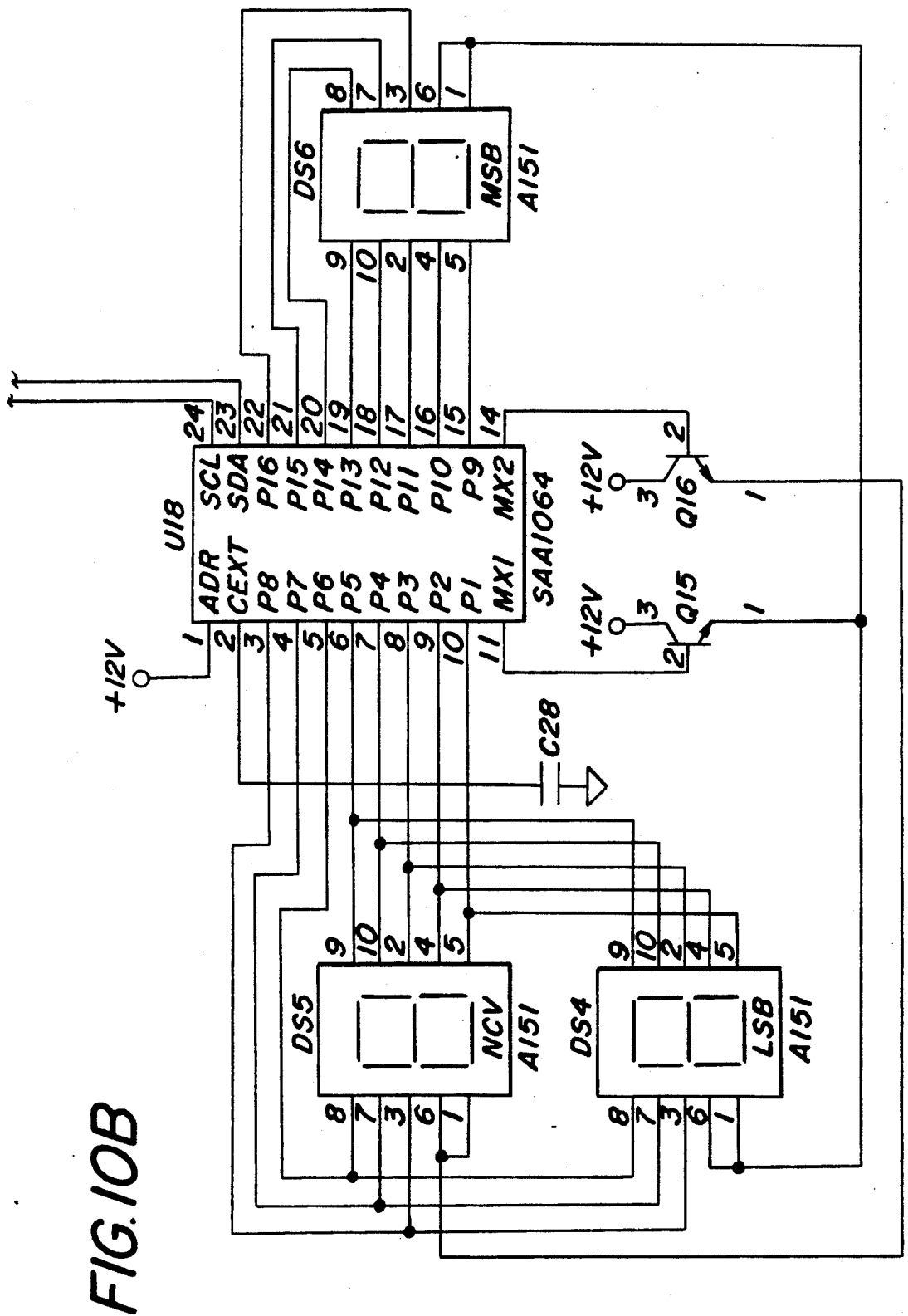

FIGS. 10A and 10B show several of the input/output and control circuits of the preferred embodiment of the present invention. Alphanumeric outputs are provided by three-digit displays, which are driven by display drivers coupled to interchip communication bus lines SCL and SDA. A pair of such three-digit display outputs is provided in the preferred embodiment. A first display, comprising displays DS1-DS3, is driven by a display driver U17. This display is used primarily to indicate temperature. An identical display, comprising seven-segment displays DS4-DS6 driven by display driver U18, displays nerve conduction parameters such as parameters related to nerve conduction velocity or elapsed time between stimulus and response. These displays are designated "TEMP" and "NCT/NCV" in FIG. 3.

Another visual output provided by the circuitry of FIG. 10A includes three indicator LEDs DS7-DS9, which are driven by displaying driver U17 in accordance with output signals from microprocessor U5 on lines SCL and SDA. As described, these displays together with switch/potentiometer R48 are desirably included in a hand-held display and control device. The function of these displays will be described in conjunction with the description of system operation.

Figure 11:
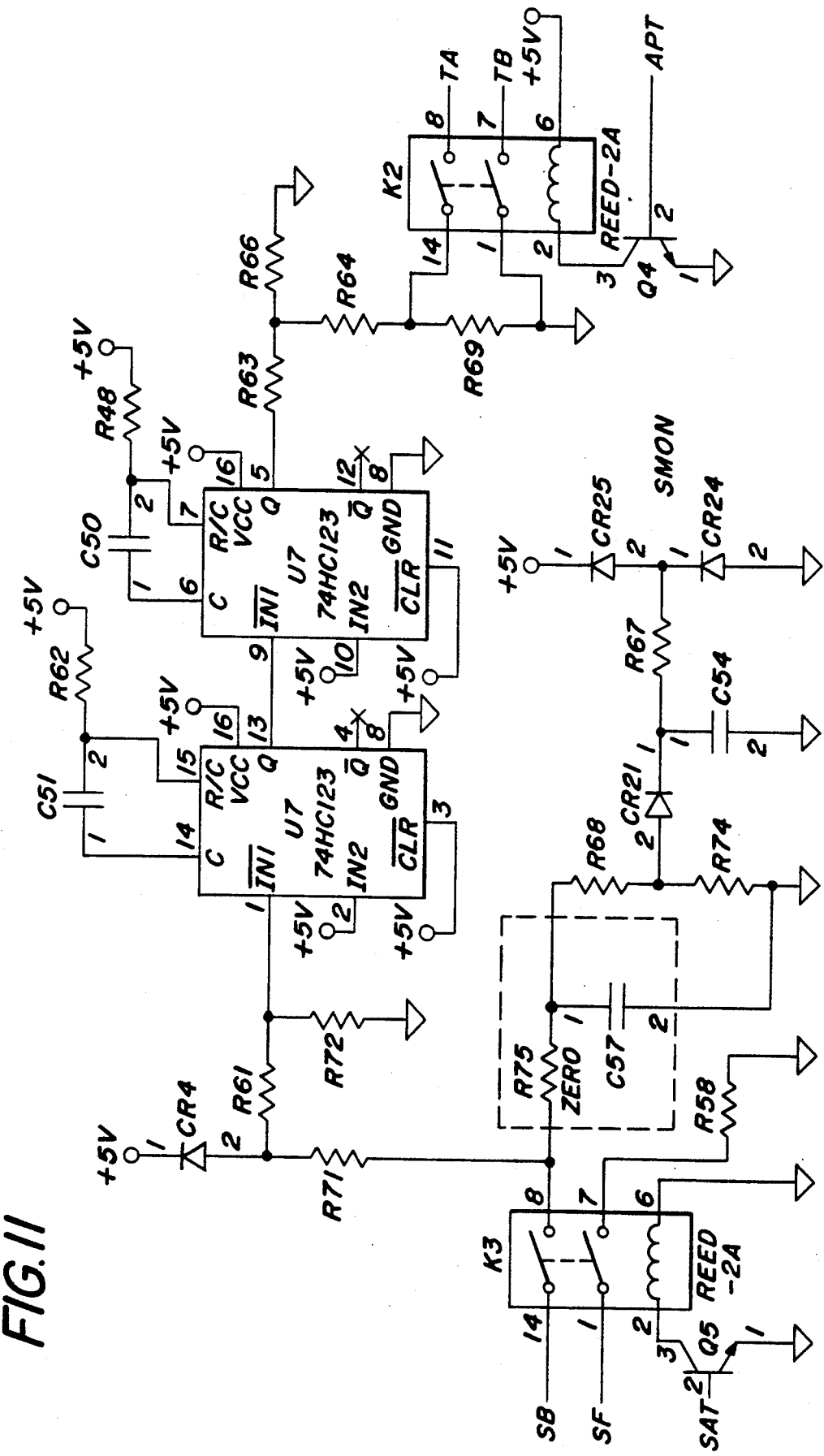
FIG. 11 is a schematic diagram of selfchecking circuitry of the preferred embodiment.

FIG. 11 is a schematic diagram of selfchecking circuitry useful for testing and/or calibrating the system. This self-checking circuit provides a simulated response signal generated by the stimulating signal, and applies it to the response signal processing circuitry to enable a determination of whether it is properly functional.

The self-testing circuitry operates under control of signals on lines APT and SAT, generated by U16 under control of output lines P1.2 and P1.3 of microprocessor U5. A high signal on line SAT actuates relay K3, which is coupled to the output lines SB and SF of the stimulating signal generator. Actuation of K3, therefore, couples stimulating signals present at the stimulating electrodes to an attenuator network comprising R75, C57, R68, R74, and C54. The output of this attenuator, SMON, is a pulse which is generally coincident with the application of a stimulating pulse to the stimulating electrodes. SMON is coupled to the ADC4 multiplexer input of U5, providing an analog signal input generally representing the amplitude of the stimulating signal generated.

A high APT signal actuates relay K2, thereby supplying a simulated response signal at the response electrodes, as follows. A stimulating pulse applied to the above-described attenuator by relay K3 is also applied to a controlled delay generating network comprising U7, configured as a pair of monostable multivibrators connected in series. A triggering input signal for the first monostable multivibrator is derived from the SB stimulating pulse line. The Q output of the first multivibrator is delayed for a predetermined period, desirably set to correspond with a nerve conduction time within the detectable range of the system. This may desirably be a normal nerve conduction time, on the order of five milliseconds. The Q output of the first multivibrator is coupled to an input of the second multivibrator which produces, after the delay imposed by the first multivibrator, a short-duration pulse simulating the response which might be received at the response electrode in normal system operation. Such pulse may be on the order of 100 microseconds duration. After attenuation by a network comprising resistors R63, R64, R66, and R69, the signal is applied by relay K2 to the inputs of the instrumentation amplifier U2, at points TA and TB. This simulated response signal is processed by the amplifier circuit to provide an ADC0 output signal to the multiplexer and A/D converter. Accordingly, by comparing the simulating output signal to the simulated input signal, in both amplitude and time, the system of the present invention is able to determine whether a substantial portion of the circuitry is properly operating. After completion of such a self-test, low signals on lines APT and SAT will return the circuit to its normal operating condition, in which it is responsive to actual nerve conduction signals received at the response electrodes.

Having thus described the apparatus of the present invention and certain features of its operation, the use of the invention and related features will now be described.

The apparatus of the invention, being portable, may be used at any desired location, including work sites and the like. Thus, for instance, an employer may desire that a large number of employees be tested. The apparatus can be brought to the employer's premises, and a large number of accurate measurements can be quickly and conveniently made on site by a minimally trained tester.

In accordance with one object of the invention, nerve conduction velocity measurements are desirably correlated with data relevant to carpal tunnel syndrome, such as personal factors (e.g. age, gender) and/or occupational or ergonomic factors. To this end, a person to be tested provides such data to the tester, such as by filling out a written questionnaire. In the preferred system, the questionnaire is provided with bar coded patent-identifying indicia such as the patient's social security number.

The tester first applies disposable electrodes to the electrode holders 26, 44, and 40. These may be standard pediatric EKG pre-gelled electrodes provided with a snap to couple them to the electrode mounting structure. The patient's arm and hand are then positioned on the apparatus so that they are in contact with the electrodes and temperature sensor as previously described. The tester then applies power to the system, by actuating switch/potentiometer R48. The system then prompts the tester to input patient identification information. In the preferred embodiment, one of the displays outputs the word BAR to indicate that the tester should scan the bar coded social security number on the patient's questionnaire. The system may then perform self-checking operations to ensure that the apparatus is functioning properly and to increase the likelihood that valid test data will be obtained. Such self-checking desirably includes hardware and software checks; in the preferred embodiment, execution of a self-checking program stored in memory 33 to operate the circuitry shown in FIG. 11 is initiated by the tester using a bar code reader to scan bar-coded information. Preferably, system self-checking also includes a determination of the quality of patient-electrode contact. In the preferred embodiment of the invention, this is performed by monitoring the signal level generated at pickup electrodes 40 in the absence of a stimulating signal. Good contact results in a low noise level, and any noise present at the electrodes will be amplified. A threshold amplifier output signal level may be established in memory, and compared with the amplifier output generated in the absence of a stimulating signal. With an appropriate threshold, an output less than the threshold indicates that good contact has been made between the finger 8 and the electrodes 40. This condition may be required to persist for a predetermined period, such as 5 seconds, and other self checking steps may be required to be successfully completed before testing may commence. Indicator DS8 indicates the occurrence of errors, such as detected during self-checking or a low battery condition. Indicator DS9 is a "ready" indicator, and is always lit when power is on unless U5 is writing to removable memory 34 or an error condition exists.

An audio and visual output indicating that contact is good and testing may commence is desirably generated at this point. Testing may be made to commence automatically upon a determination of good contact.

Upon initiation of testing, stimulating signal generator 42 commences generating signals at stimulating electrodes 44, which are automatically repeated at periodic intervals (e.g. one second) under control of microprocessor U5, at an amplitude determined by amplitude control 50. Indicator DS7 is lit simultaneously with the application of each stimulating signal. After each application of a stimulating signal, the response signal at pickup electrodes 40 is processed. As has been described, during an initial period the amplifier is decoupled from the electrodes to inhibit its response to spurious signals; thereafter the response signal is amplified, converted to digital form and input to the CPU. In accordance with an important object of the invention, waveform data relating to received nerve conduction signals is stored in memory. In the preferred embodiment, this data is stored by sampling at periodic intervals and storing data relating to the signal amplitude at the time each sample is taken. Applicants have used a separation of 14 cm between stimulating electrodes 44 and pickup electrodes 40. A normal nerve conduction velocity of 30–40 meters per second over this separation would correspond to a normal elapsed time in the range of 3.5–4.7 milliseconds. Nerve conduction velocities in practice may vary over the range of about 10–80 meters per second, corresponding to elapsed times in the range of about 1.8–14 milliseconds. Applicants have found that response waveforms over this time range may be adequately analyzed by taking 200 8-bit samples at 70 microsecond intervals.

The system of the preferred embodiment includes several features directed to reliable, substantially automated use. These features include requiring predetermined response signal characteristics in order for a test result of be considered acceptable, and automatically terminating the test upon receipt of response signals having such characteristics. In the preferred embodiment, a number of stimulating signals must result in similar response signals in order for a test to be considered reliable. While a variety of response signal characteristics may be evaluated for similarity to varying degrees, applicants have found that results may be deemed reliable if four response signals have peak amplitudes falling within the same sampling interval. This result-qualification method is implemented as follows. At the start of testing, an array of 200 memory locations is initialized to a value of 4. Sampled amplitude data from the pickup electrodes 40 is stored in a 200 byte array in memory. In accordance with a stored program, the CPU determines the peak value of the sampled amplitude data. The CPU then compares the peak value with stored threshold values to determine whether the received waveform is to be considered a valid response. Desirably, the peak value is required to lie between an upper and a lower threshold for the response to be considered valid. If the peak value of the stored amplitude data is within the allowed range, the element of the 200 location array corresponding to the sample interval in which the peak occurred is decremented. If the peak value is below a lower threshold, the stimulating signal amplitude may be adjusted (by adjusting R48 or automatically under program control) until valid response signals are received.

In order to provide high reliability to the substantially automated measurement, the system of the present invention requires that a predetermined number of test pulses provide corresponding nerve conduction velocity measurements. Applicants have found that adequate reliability is obtained when four response waveforms have their peaks in the same sample interval. It is for this reason that each element of the 200 element array is initialized to a value of 4, as described; the initial value may be selected as desired to optimize reliability of data and testing time. If four peaks occur in the same sample interval, the array element corresponding to this interval will be decremented to 0, and this condition may be detected and deemed to be a successful test. An upper limit may be established within which the four matching responses must be obtained to be considered valid. Applicants have found an upper limit of about 600 pulses to be adequate. To assist the tester in determining the progress of the test, a display may be generated corresponding to the number of response signals having a peak in the same sample interval which have been received.

At the successful conclusion of a test, the system ceases generating stimulating pulses and may generate a variety of desired outputs such as an audio signal indicating completion of the test or a numeric display indicating the peak sample interval, elapsed time, or computed nerve conduction velocity. Test data is then saved, preferably by writing such data to removable memory 34, for future analysis or confirmation of test results or comparison with data taken at other times. Such saved data desirably includes patient identifying data, test condition data such as the date and time of the test, data identifying the particular piece of equipment used to make the test, and test-identifying data such as a sequential number indicating the number of tests which have been performed on that piece of equipment. The saved data also includes data relating to the test results, such as temperature and measured elapsed time or computed nerve conduction velocity. Desirably, the data also includes waveform data relating to a successful test. Applicants have found it acceptable to save only the waveform data relating to the last stimulating signal which produced a response peak in the same sample time interval as the preceding peaks. Thus, to save memory in both the main memory 33 and the removable memory 34, the system of the present invention overwrites the data in the 200 sample amplitude data array with each pulse. When four pulses have yielded peaks in the same sample interval, the last waveform occurring prior to determination of a successful test may be considered to be a reliable test result.

The above method for automatically determining elapsed time based on a number of automatically generated stimulus-response events has a number of advantages over alternatives. For example, alternatively amplitude data arrays could be generated for a number of successive samples, and the arrays averaged or the like to produce an averaged waveform which may be analyzed to determine its peak or other parameters. For instance, data pertaining to a predetermined number of successive pulses may be stored and averaged. However, spurious signals such as caused by loss of patient-electrode contact may radically affect the stored average value and lead to incorrect results. This situation might be minimized by taking a sufficiently large number of samples, but not necessarily, and the time required to do so may provide a serious drawback to such a system.

Nerve conduction monitoring is desirably performed on both the left and right hands of the patient. After successfully testing a patient, the above process may be repeated to test additional patients. After data from successful tests of one or more patients has been obtained, it must be transmitted to a person such as a neurologist who is qualified to interpret the test results and make any diagnosis or treatment recommendation required. This may entail delivery to the neurologist of the removable memory device itself and the patient questionnaires having associated personal and ergonomic data regarding the patient at the time of testing. Alternatively, the data may be telecommunicated, such as by modem. To this end, the port 62 may be coupled to a modem as an I/O device 64. Also, the saved data may be transferred to a computer by port 62; many computers can communicate with the testing apparatus over the RS-232 port provided by U4. In a preferred method, data is transferred to a computer such as a PC type computer via port 62. Upon successful transfer of data, the testing apparatus memory in which the test data was stored is erased, to permit further use. The data in the computer may be stored on a removable storage medium for delivery, or may be telecommunicated, to the neurologist for analysis. Such a method may eliminate the need for a removable memory. Likewise, the patient questionnaire data may be delivered, telecommunicated by facsimile transmission, or converted to encoded digital data and telecommunicated to the neurologist. In either event, the test results are matched with the questionnaire data for a particular patient for analysis by the neurologist.

Carpal tunnel syndrome is a cumulative trauma disorder; normal activity injures the median nerve in the carpal tunnel to varying degrees, and the injury is repaired to varying degrees by the body's natural healing processes during inactivity. If the injury is effectively fully repaired on an ongoing basis, nerve conduction remains at a desirable level and carpal tunnel syndrome does not develop. If, however, the healing effected during inactivity is insufficient to fully heal the median nerve, its condition becomes progressively worse until carpal tunnel syndrome develops. Various personal and ergonomic factors affect both the amount of injury to which the median nerve is subjected in a particular individual and the capacity of that individual to heal such injury. For instance, healing capacity decreases with age and is smaller in women than in men, primarily due to hormonal changes with resultant fluid retention and the cross-section size of the carpal tunnel due to small wrist size in some women. Also, individuals are subjected to different levels of ongoing nerve injury depending on the requirements of their job, their recreational activities, and the like.

Applicants believe that the likelihood of an individual developing carpal tunnel syndrome may be evaluated in accordance with such personal and ergonomic factors, and in accordance with the condition of the individual's median nerve at the time of such evaluation. The testing system of the present invention is well adapted to determining nerve condition. It is generally accepted among those knowledgeable in the art that the nerve conduction velocity of the sensory nerves is a sensitive indicator of nerve condition. Sensory nerves deteriorate at a much lower level of cumulative median nerve injury than do the motor nerves, and thus provide an earlier indication of such injury. It is for this reason that the preferred testing system measures sensory nerve conduction velocity through the carpal tunnel, even though the signal levels obtained are much smaller and thus more difficult to process than motor nerve signals.

Accordingly, the system of the present invention permits early evaluation of the likelihood of developing carpal tunnel syndrome; and by successive evaluation at different times, the existence and extent of nerve deterioration can be determined. It also permits intervention and treatment at a time when minor changes may be effective in halting or reversing nerve deterioration. For instance, a recommendation may be made that an individual change his work practices (e.g. more rest or more frequent rest from use of the hands) or alter his recreational activities (e.g. minimize sports which tend to injure the median nerve).

The system of the invention further permits feedback control of the treatment recommendations. For instance, a patient may be given an initial evaluation and treatment recommendation. A subsequent test will show both the extent to which the treatment recommendation was followed (in the questionnaire data) and the effect of that treatment on median nerve condition in that individual (in the change in nerve conduction velocity measured). Accordingly, the individual's treatment may be modified as necessary to achieve the desired effect on nerve condition. By rendering initial and follow-up testing easy, inexpensive, and convenient, and by providing reliable measurements using standardized apparatus and monitoring parameters, the apparatus of the invention is well adapted for use in such a method.

The same advantages allow for optimization of diagnostic accuracy and treatment recommendation based upon synthesizing the results of individual test and treatment response data. While a variety of personal and ergonomic factors are known to have some relationship to the development of carpal tunnel syndrome, the nature and extent of the relationship and the interrelation of such factors is not generally well understood. Moreover, the optimum treatment recommendation for a particular patient having particular such personal and ergonomic factors is largely indeterminate due to lack of data upon which to base such a recommendation, and treatment recommendation at present is typically made on an ad hoc basis by the physician on the basis of intuition and general notions developed over the course of his practice.

The system of the present invention, by facilitating widespread data acquisition relating both to diagnosis and treatment efficacy, by facilitating such data acquisition in a reliable and uniform manner, and by centralizing the data in the hands of physicians who must be employed in any event to diagnose and recommend treatment for individual patients, also permits a substantial improvement in diagnosis and treatment recommendation. In the preferred system of the invention, data from a number of tests is stored in a database and operated upon by an expert system computer program, preferably an artificial intelligence computer program, to generate diagnosis and treatment information for use in a particular case and to update the generated information in accordance with the changing contents of the database. The preferred fields of data in the database include nerve conduction velocity-related data, personal data, and ergonomic data. Nerve conduction velocity data is preferably generated by the apparatus and method described herein. Personal data fields desirably include fields selected from the group consisting of dominant hand; age; gender; height; weight; wrist circumference, height, and width; diabetes conditions; thyroid conditions; estrogen level; carpal tunnel symptoms; arm symptoms; and avocations involving repetitive use of the hands or arms (such as computer use, knitting, and the like). Ergonomic or occupational data fields desirably include fields selected from the group consisting of occupational requirements for activities involving repetitive use of the hands or arms; grip force, pinch force; wrist flexion; palm pressure; vibration; glove use; exposure to cold; and wage incentives such a piece work wages.

While preferred embodiments of the invention have been described, variations will no doubt occur to those skilled in the art without departing from the spirit and scope of the invention.

What is claimed is:

1. Patient nerve condition monitoring apparatus comprising:
    a pair of stimulating electrodes adapted to apply an electrical stimulating signal to a patient;
    a pair of pickup electrodes adapted to receive a response electrical signal from the patient induced by a stimulating signal; and
    an electrode supporting structure supporting said stimulating electrodes in a location adapted to contact a portion of said patient's arm adjacent the median nerve and supporting said pickup electrodes in a location adapted to contact a portion of the patient's hand adjacent the median nerve when said stimulating electrodes are in contact with the patient's arm, so that application of an electrical stimulating signal by said stimulating electrodes to the patient's arm induces a sensory nerve conduction signal in the patient which is propagated along a median nerve conduction path extending from a location in the patient's arm adjacent said stimulating electrodes to a location in the patient's hand adjacent said pickup electrodes to produce a detectable sensory nerve response electrical signal at said pickup electrodes, and the length of the nerve conduction path is substantially permanently fixed by said electrode supporting structure.

2. Apparatus according to claim 1, wherein said electrode supporting structure includes surfaces which are shaped to locate the patient's arm and hand with respect to said stimulating and pickup electrodes respectively.

3. Apparatus according to claim 2, wherein said electrode supporting structure includes a curved surface adapted to generally conform to a human forearm, and said stimulating electrodes are mounted to said curved surface.

4. Apparatus according to claim 1, wherein said electrode supporting structure includes a first surface adapted to receive a human forearm in contact with it and a second surface adjacent said first surface and adapted to receive a human hand in contact with it, said first surface being disposed at an angle between 90° and 180° with respect to said second surface so that movement of a patient's forearm and hand when in contact with said first and second surfaces is inhibited.

5. Apparatus according to claim 1, further comprising a stimulating signal generator coupled to said stimulating electrodes and a response signal processor coupled to said pickup electrodes for processing response signals received by said pickup electrodes.

6. Apparatus according to claim 5, wherein said electrode supporting structure comprises a housing containing said stimulating signal generator and said response signal processor circuit.

7. Apparatus according to claim 1, wherein at least some of said electrodes are resiliently mounted to said electrode supporting structure.

8. Apparatus according to claim 1, further including a temperature sensor supported by said electrode supporting structure and adapted to contact said patient when said patient is in contact with said electrodes.

9. Patient nerve condition monitoring apparatus for monitoring nerve conduction through the carpal tunnel of a patient comprising:
    a pair of stimulating electrodes adapted to be coupled to a patient's arm;
    a stimulating signal generator coupled to said stimulating electrodes;
    a pair of pickup electrodes having a permanent predetermined spatial relationship to said stimulating electrodes, said pickup electrodes being adapted to be coupled to the patient's hand so as to receive response signals generated in response to application of a stimulating signal to the patient's arm; and
    a response signal processor coupled to said pickup electrodes, said processor including means for determining the elapsed time between the application of a stimulating signal to said stimulating electrodes and the receipt of a predetermined response signal by said pickup electrodes.

10. Apparatus according to claim 9, wherein said processor includes a CPU, a memory coupled to said CPU for storing data and for storing operating programs to be executed by said CPU, and an analog-to-digital converter having at least one input for receiving analog signals and an output coupled to said CPU, said converter producing at its output digital signals which are related to analog signals received at said converter input.

11. Apparatus according to claim 10, wherein said stimulating signal generator includes a control input coupled to said CPU, and said CPU controls the generation of stimulating signals by said generator.

12. Apparatus according to claim 10, wherein said pickup electrodes are coupled to an input of said converter.

13. Apparatus according to claim 12, further comprising an amplifier having inputs coupled to said pickup electrodes and an output coupled to a converter input.

14. Apparatus according to claim 13, wherein said amplifier is a bandpass amplifier.

15. Apparatus according to claim 13, further including means for inhibiting the response of said amplifier to signals which are unrelated to nerve conduction signals.

16. Apparatus according to claim 15, wherein said amplifier response inhibiting means includes means for inhibiting the response of said amplifier to input signals occurring at predetermined times with respect to the time of generation of stimulating signals.

17. Apparatus according to claim 16, wherein said amplifier response inhibiting means includes a switch coupled to said amplifier, said switch having a control input coupled to said CPU.

18. Apparatus according to claim 10, wherein said memory includes removable static memory.

19. Apparatus according to claim 10, wherein said predetermined response signal is the peak value of the response signal received by said pickup electrodes.

20. Apparatus according to claim 10 wherein said CPU stores data in said memory relating to nerve conduction through the carpal tunnel of the patient.

21. Apparatus according to claim 20, wherein said stored data includes data relating to said elapsed time.

22. Apparatus according to claim 20, wherein said stored data includes data representing the response waveform received by said pickup electrodes in response to a stimulating signal applied to said stimulating electrodes.

23. Apparatus according to claim 20, wherein said apparatus includes a temperature sensor coupled to said patient and producing an output related to the patient's body temperature, and said stored data includes patient body temperature data.

24. Apparatus according to claim 20, wherein said CPU stores data in said memory relating to the patient being monitored.

25. Apparatus according to claim 20, wherein said CPU stores data in said memory relating to the apparatus being used in said patient monitoring.

26. Apparatus according to claim 10, wherein said processor includes one or more ports coupled to said CPU and one or more input/output devices coupled to said port(s).

27. Apparatus according to claim 26, wherein said input/output devices include a bar code reader.

28. Apparatus according to claim 26, wherein said input/output devices includes at least one alphanumeric display.

29. Apparatus according to claim 28 wherein said display displays information relating to patient nerve condition.

30. Apparatus according to claim 28, wherein said display displays information to prompt a user in proper use of the apparatus.

31. Apparatus according to claim 10, further including means for controlling the characteristics of stimulating signals produced by said stimulating signal generator.

32. Apparatus according to claim 31, wherein said signal characteristic controlling means is manually operable.

33. Apparatus according to claim 10, wherein said processor includes means for substantially automatically controlling said generation of stimulating signals and said determination of elapsed time.

34. Apparatus according to claim 33, further including a self-checking circuit for generating synthetic response signals and coupling synthetic response signals to said response signal processor.

35. Apparatus according to claim 33, wherein said control means includes means for determining the quality of contact between said patient and said electrodes.

36. Apparatus according to claim 35, wherein said contact quality determining means includes means for comparing a signal received at said pickup electrodes with a threshold signal value.

37. Apparatus according to claim 33, wherein said control means includes means for automatically and repeatedly generating stimulating electrical signals and monitoring response signals, and for terminating said generation and monitoring upon the occurrence of predetermined conditions.

38. Apparatus according to claim 37, wherein said predetermined conditions are conditions of response signals received by said pickup electrodes.

39. Apparatus according to claim 38, wherein said predetermined response signal conditions are the occurrence of a plurality of similar response signals in response to a plurality of successive stimulating signals.

40. Apparatus according to claim 39, wherein said response signals are similar in the time of occurrence of a predetermined response signal characteristic with respect to the time of the stimulating signal producing said response signal.

41. Apparatus according to claim 40, wherein said predetermined response signal characteristic is the peak amplitude of said response signal.

42. Apparatus according to claim 39, wherein said predetermined response signal conditions are the occurrence of similar response signals in response to about four successive stimulating signals.

43. A method of monitoring conduction velocity of nerves passing through the carpal tunnel of a patient comprising the steps of:

a. providing a pair of stimulating electrodes and a pair of pickup electrodes having a predetermined permanent spatial relationship to said stimulating electrodes;

b. coupling said pickup electrodes to the hand of the patient and coupling said stimulating electrodes to the forearm of the patient;

c. applying a stimulating electrical signal to said stimulating electrodes; and d. determining the elapsed time between the application of a stimulating signal to the stimulating electrodes and the occurrence of a predetermined characteristic of the response signal produced at said response electrodes in response to said stimulating signal.

44. A method according to claim 43, wherein said coupling step b includes bringing the arm and hand of said patient into contact with an electrode supporting structure which supports said stimulating and pickup electrodes.

45. A method according to claim 44, further comprising the step of limiting the movement of the patient's arm and hand with respect to said electrode supporting structure.

46. A method according to claim 43, further comprising the step of measuring the body temperature of said patient.

47. A method according to claim 43, further comprising the step of monitoring the quality of coupling between said patient and said electrodes.

48. A method according to claim 43, wherein steps c and d are performed automatically and repeatedly until the occurrence of a predetermined event.

49. A method according to claim 48, wherein said predetermined event is the determination of similar elapsed times in response to the application a plurality of stimulating signals.

50. A method according to claim 48, further comprising the step of storing data relating to said nerve conduction velocity monitoring.

51. A method according to claim 50, wherein said data storing step includes storage of data relating to said elapsed time.

52. A method according to claim 50, where said data storing step includes storing patient-identifying data.

53. A method according to claim 50 wherein said data storing step includes storing data relating to the circumstances under which said monitoring is performed.

54. A method according to claim 50, wherein said data storing step includes storing data representing a response signal waveform received at said response electrodes in response to said stimulating signal.

* * * * *

UNITED STATES PATENT AND TRADEMARK OFFICE
CERTIFICATE OF CORRECTION

PATENT NO. : 5,215,100

DATED : June 1, 1993

INVENTOR(S) : Lawrence K. Spitz; Scott Jaeger; Scott N. Musser

It is certified that error appears in the above-identified patent and that said Letters Patent is hereby corrected as shown below:

Col. 1, line 58, delete "ormitigate" and insert therefor -- or mitigate--.

Col. 20, line 58, delete "predetermined permanent" and insert --permanent predetermined--.

Signed and Sealed this

Twelfth Day of April, 1994

Attest:

BRUCE LEHMAN

Attesting Officer

Commissioner of Patents and Trademarks